(12) United States Patent
Lawrie (10) Patent No.: US 11,986,258 B2
(45) Date of Patent: May 21, 2024

(54) DEPTH LIMITER FOR ROBOTICALLY ASSISTED ARTHROPLASTY

(71) Applicant: Zimmer, Inc., Warsaw, IN (US)

(72) Inventor: Charles M. Lawrie, St. Louis, MO (US)

(73) Assignee: Zimmer, Inc., Warsaw, IN (US)

( * ) Notice: Subject to any disclaimer, the term of this patent is extended or adjusted under 35 U.S.C. 154(b) by 228 days.

(21) Appl. No.: 17/492,050

(22) Filed: Oct. 1, 2021

(65) Prior Publication Data

US 2022/0104901 A1 Apr. 7, 2022

Related U.S. Application Data

(60) Provisional application No. 63/088,713, filed on Oct. 7, 2020.

(51) Int. Cl.
*A61B 34/30* (2016.01)
*A61B 17/16* (2006.01)
*A61B 90/00* (2016.01)

(52) U.S. Cl.
CPC .......... *A61B 34/30* (2016.02); *A61B 17/1633* (2013.01); *A61B 90/03* (2016.02); *A61B 2090/034* (2016.02); *A61B 2090/062* (2016.02)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1633; A61B 17/1662; A61B 17/1664; A61B 17/1666; A61B 17/1684; A61B 34/30; A61B 34/32; A61B 34/35; A61B 34/37; A61B 90/03; A61B 2090/033; A61B 2090/034; A61B 2090/036

See application file for complete search history.

(56) References Cited

U.S. PATENT DOCUMENTS

| 9,788,880 | B2 * | 10/2017 | Barsoum | A61B 17/16 |
| 2005/0043805 | A1 * | 2/2005 | Chudik | A61B 17/1684 |
| | | | | 623/908 |
| 2011/0257746 | A1 * | 10/2011 | Michelson | A61B 17/56 |
| | | | | 623/17.11 |
| 2020/0297357 | A1 * | 9/2020 | Cameron | A61B 17/162 |
| 2022/0104901 | A1 * | 4/2022 | Lawrie | A61B 34/30 |

FOREIGN PATENT DOCUMENTS

| CN | 112932668 | A | * | 6/2021 | .......... A61B 17/162 |
| EP | 3827760 | A1 | * | 6/2021 | .......... A61B 17/162 |
| JP | 2021084037 | A | * | 6/2021 | .......... A61B 17/162 |
| JP | 7239545 | B2 | * | 3/2023 | .......... A61B 17/162 |
| WO | WO-2018156089 | A1 | * | 8/2018 | ......... A61B 17/1637 |

* cited by examiner

*Primary Examiner* — Eric S Gibson
(74) *Attorney, Agent, or Firm* — SCHWEGMAN LUNDBERG & WOESSNER, P.A.

(57) ABSTRACT

A robotically controlled depth limiter for a reamer, the depth limiter including a cylindrical housing configured to encompass a portion of a driveshaft of a reamer. The cylindrical housing can define a bore extending therethrough. The depth limiter can include a depth stop engaging the cylindrical housing within the bore, and define an opening configured to receive the driveshaft of the reamer. The depth stop can be configured to receive a signal via processing circuitry of a robotic arm to operate the depth stop to limit distal translation of the driveshaft relative to the cylindrical housing to control a cutting depth of the reamer.

17 Claims, 8 Drawing Sheets

DEPTH LIMITER FOR ROBOTICALLY ASSISTED ARTHROPLASTY

CLAIM OF PRIORITY

This application claims the benefit of U.S. Provisional Patent Application Ser. No. 63/088,713, filed on Oct. 7, 2020, the benefit of priority of which is claimed hereby, and which is incorporated by reference herein in its entirety

TECHNICAL FIELD

The present application pertains generally, but not by way of limitation, to devices and methods for robotically-assisted surgical procedures, such as those involving the use of articulating robotic arms to hold or position surgical instruments.

BACKGROUND

In preparation for a hip arthroplasty (hip replacement) procedure, for example, several fluoroscopic (x-ray) images of the hip joint are typically obtained as a part of a pre-operative evaluation. The resulting radiographic images can be used to create a pre-operative plan. The pre-operative plan can include, among others details, a selection of an implant, various limb measurements, and the reaming depth needed to prepare an acetabulum to receive the implant. A surgeon often also takes one or more intra-operative fluoroscopic images to confirm the accuracy of certain aspects of pre-operative plan, such as the reaming depth. A cutting instrument, such as a reamer, can then be operated by the surgeon to shape the acetabulum.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims.

During an arthroplasty procedure, a reamer or other cutting device, can be used to shape a bone surface of a patient, to prepare the bone surface to receive an implant. First, an access incision can be made in a surgical region of the patient, through which a reamer can access the bone surface. Because it may be difficult to manually hold or position a reamer along a certain trajectory for an extended length of time, surgical arms can be used to hold the cutting device while reaming or other aspects of the surgical procedure are performed. Some surgical arms can be electromechanically adjustable, such that they can be moved about one or more axes using a control system, to positon the arm and the cutting device pre-operatively or intra-operatively. Precisely reaming the acetabulum to the correct depth can be critical to the success of a hip replacement procedure, as under-reaming or over-reaming can lead to improper biomechanics resulting in bone fractures or acute failure of the replacement joint.

A robotic arm can be used to increase the accuracy of the reaming process by holding and positioning a reamer in a desired orientation relative to a patient's anatomy during a surgical procedure. A reamer is typically constrained along a trajectory by an end effector coupled to a distal end of the robotic arm. The reamer can be manually advanced, while guided along a fixed trajectory by the end effector, to a calculated cutting depth by a surgeon. In some procedures, a surgeon can also electronically advance the reamer to the calculated cutting depth using a control system of an electromechanical robotic arm.

However, if the reamer is to be advanced manually, the cutting device sometimes includes a depth stop positioned on a cutting head of the reamer to prevent over-reaming. The depth stop typically extends radially outward from the cutting head, reducing visibility for a surgeon operating the cutting device. The depth stop can also have a fixed, or non-adjustable design integrated with the cutting head, which can require a surgeon the change the cutting head intra-operatively, lengthening the procedure. If the cutting device is to be robotically advanced, a virtual three-dimensional model of the target surgical area is typically created using, for example, CT scans. This can add significant preparation time and expense for both the patient and the surgeon, as the patient must undergo more extensive imaging than is typically required. Further, if the surgeon is to guide the reamer based on a virtual model, the reamer must be advanced very slowly, often a millimeter at a time, in order to prevent over-reaming.

This disclosure can help to address these issues, among others, by providing a depth limiter for a surgical reamer capable of precisely limiting a maximum cutting depth of a reamer based on limited pre-operative or intra-operative fluoroscopic imaging with limited robotic assistance. The reamer, together with the depth limiter and the robotic arm, can precisely ream the bone surface without requiring the use of a fixed depth stop integrated into the distal end of the reamer, or the creation of a virtual model and the use of a tracking system for robotic guidance of the robotic arm. The depth limiter disclosed herein can be configured to receive radiographic information through fluoroscopy to adjustably limit a maximum reaming depth of the reamer. The depth limiter can help a surgeon to reach a calculated cutting depth quickly and precisely, without extensive imaging, and with minimal robotic assistance. The depth limiter can thereby reduce the length of a hip replacement procedure while reducing the risk of under or over-reaming a patient's acetabulum during hip arthroplasty.

The above overview is intended to provide an overview of subject matter of the present patent application. It is not intended to provide an exclusive or exhaustive explanation of the invention. The description below is included to provide further information about the present patent application.

While the following examples are discussed in view of hip replacement procedures, the described robotic arm, end effector, and reamer can be utilized in other similar arthroplasty procedures. For example, the robot and the end effector including the depth limiter and the reamer can be utilized to ream a glenoid during a shoulder arthroplasty procedure. Accordingly, the depth limiter, in combination with the robotic arm, can provide similar benefits in a shoulder arthroplasty procedure, such as with respect to reaming a glenoid, as described throughout with regard to hip arthroplasty.

Figure 1A:
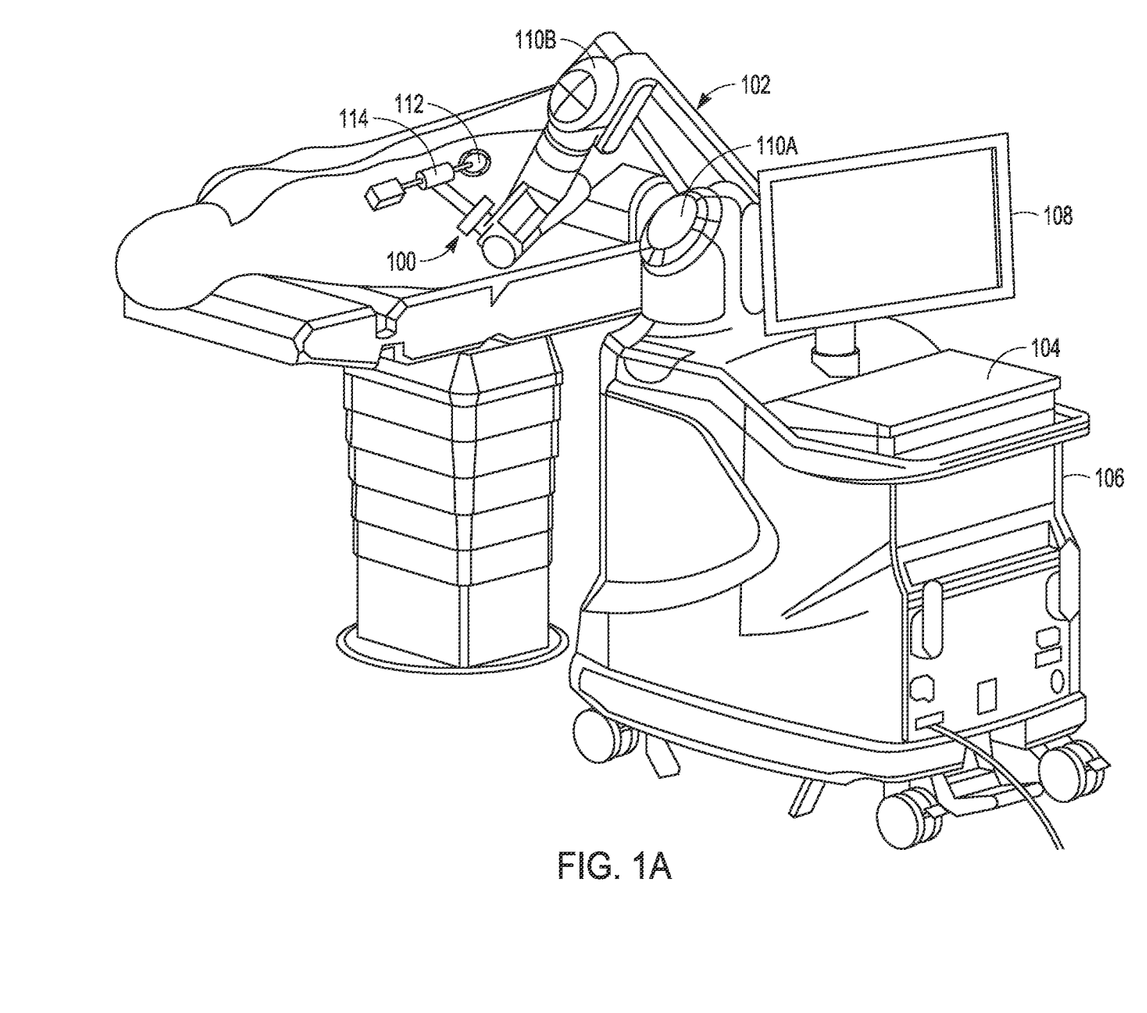
FIG. 1A illustrates an isometric view of an example of an end effector coupled to a robotic arm including a control system, in accordance with at least one example of the present application.
Figure 1B:
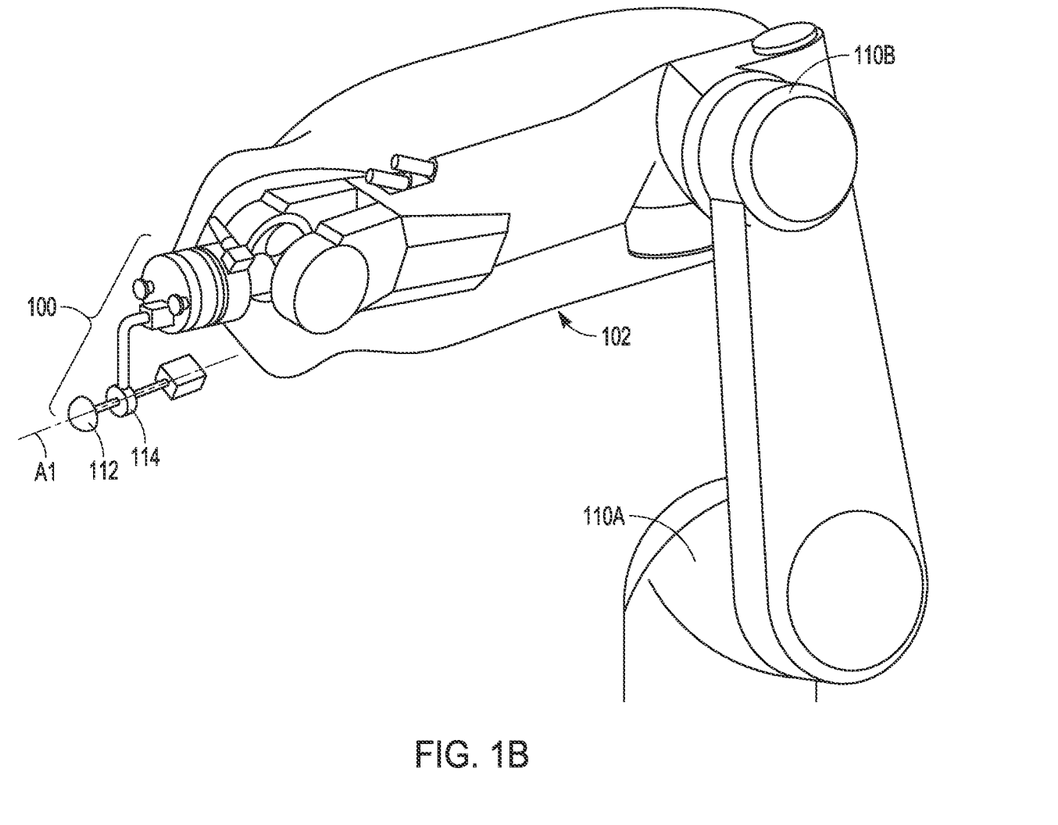
FIG. 1B illustrates an isometric view of an example of an end effector coupled to a robotic arm, in accordance with at least one example of the present application.

FIG. 1A illustrates an isometric view of an example of an end effector coupled to a robotic arm including a control system, in accordance with at least one example of the present application. FIG. 1B illustrates an isometric view of an example of an end effector coupled to a robotic arm, in accordance with at least one example of the present application. Also shown in FIG. 1B is a central axis A1. FIGS. 1A-1B are discussed below concurrently.

As illustrated in FIGS. 1A-1B, an end effector 100 can be coupled to a robotic arm 102. The robotic arm 102 can be controlled by a surgeon with various control devices or systems. For example, a surgeon can use a control system 104 (e.g., a controller that is processor-implemented based on machine-readable instructions, which when implemented cause the robotic arm to move automatically or to provide force assistance to surgeon-guided movement) to guide the robotic arm 102. The control system 104 can include a computing system 106, which can communicate with a display screen 108. A surgeon can use anatomical imaging displayed on the display screen 108 to guide and position the robotic arm 102. Anatomical imaging can be provided to the display screen 108 from various imaging sources, such as one or more cameras positioned on the end effector 100, or from a C-arm providing preoperative or intraoperative fluoroscopy.

The control system 104 can electrically operate the robotic arm 102 and the end effector 100 using processing circuitry. The control system 104 can include at least a memory, a processing unit, and user input devices, as will be described below. The control system 104 can be a separate standalone system, or can be integrated into robotic arm 102 and the control system 104. The control system 104 can also include human interface devices for providing images for a surgeon to be used during surgery. Human interface devices can provide images, such as three-dimensional images of the acetabulum and femur, the humerus and glenoid, other bones or joints, or the like. Human interface devices can include associated input mechanisms, such as a touch screen, foot pedals, or other input devices usable in a surgical environment.

The control system 104 can receive pre-operative, intra-operative, or post-operative medical images. These images can be received in any manner and the images can include, but are not limited to, computed tomography (CT) scans, magnetic resonance imaging (MRI), two-dimensional x-rays, three-dimensional x-rays, ultrasound, or the like. These images in one example can be sent via a server as files attached to an email. In another example, the images can be stored on an external memory device such as a memory stick and coupled to a USB port of the robotic system to be uploaded into the processing unit. In yet other examples, the images can be accessed over a network by the control system 104 from a remote storage device or service.

In some examples, after receiving one or more images, the control system 104 can generate one or more virtual models related to a surgical area. Alternatively, the control system 104 can receive virtual models of the anatomy of the patient prepared remotely. Specifically, a virtual model of the anatomy of a patient can be created by defining anatomical points within the image(s) and/or by fitting a statistical anatomical model to the image data. The virtual model, along with virtual representations of implants, can be used for calculations related to the desired location, height, depth, inclination angle, or version angle of an implant, stem, acetabular cup, glenoid cup, surgical instrument, or the like. In another procedure type, the virtual model can be utilized to determine insertion location, trajectory and depth for inserting an instrument, such as an instrument received or integrated into the end effector 100. In a specific example, the virtual model can be used to determine a reaming angle and a maximum reaming depth for a reamer, relative to an acetabulum of a pelvis and a depth for reaming into the pelvis to place an acetabular implant.

The robotic arm 102 can also include two or more articulating joints 110A and 1101B. The articulating joints 110A and 110B can be capable of pivoting, rotating, or both, to provide a surgeon with wide range of axial or radial adjustment options for the robotic arm 102. The robotic arm 102 can be coupled to a surgical instrument, such as a reamer 112, via the end effector 100. The end effector 100 of the robotic arm 102 can receive or include various surgical instruments, for example, a guide tube, a holder device, a gripping device such as a pincer grip, a burring device, a reaming device, an impactor device such as a femoral or humeral head impactor, a pointer, a probe, a collaborative guide or holder device as described herein, or the like.

The reamer 112 can define the central axis A1. The reamer 112 can include a depth limiter 114. The depth limiter 114 can be configured to engage with various pre-existing types or styles of the reamer 112. The end effector 100, including the reamer 112 and the depth limiter 114, can be coupled to and extend distally from, the robotic arm 102. With the articulating joints 110A and 1101B of the robotic arm 102 being immobilized (e.g., not moving) or locked in place, the depth limiter 114 of the end effector 100 can engage the reamer 112 to position the reamer 112 along a planned surgical trajectory, while also limiting movement of the reamer 112 along the central axis A1. The depth limiter 114 can be configured to receive a signal via the processing circuitry of the control system 104, and in response, adjustably limit axial distal translation of the reamer 112 to adjustably control the maximum cutting depth of the reamer 112.

In the operation of some examples, during a hip arthroplasty, the robotic arm 102 can position the end effector 100, including the reamer 112 and the depth limiter 114 at the acetabulum or within the acetabular cavity of a patient. A surgeon can take a number of fluoroscopic images using, for example, a C-arm. The resulting radiographic images can be used to calculate a distance between a distal end of the reamer 112 and a desired maximum cutting depth into the acetabulum. The surgeon can then, using the processing circuitry of the control system 104, send a signal including the maximum cutting depth, to the depth limiter 114. In response, the depth limiter 114 can adjust the maximum axial travel of the reamer 112 to correspond to the maximum cutting depth. The surgeon can then activate the reamer 112 and translate the reamer distally along the central axis A1 until the depth limiter 114 prevents further axial translation of the reamer 112. The surgeon can also take additional fluoroscopic images and re-adjust the depth limiter 114 for subsequent reaming as needed. After reaming is completed, the end effector 100, including the reamer 112 and depth limiter 114, can be decoupled from the robotic arm 102 and sterilized for a subsequent procedure.

As such, the robotic arm 102, together with the reamer 112 and the depth limiter 114 can provide a number of benefits to a patient. The ability of the robotic arm 102 to be adjustably pivoted, rotated, or otherwise articulated intra-procedurally, either autonomously or cooperatively with the operator, to adjust a cutting angle or trajectory of the reamer 112 can allow for greater bone preservation than would otherwise be possible with a fixed trajectory.

The robotic arm 102 can control the position, movement, and force applied by the reamer 112 more precisely and steadily than a human hand, such that the reamer does not require a fixed depth stop to prevent over-reaming of a bone surface. This can reduce the cost of producing the reamer 112, increase the visibility of the surgical area for an operator, and further decrease the amount of space needed within an incision for a cutting instrument to operate. Additionally, the depth limiter 114 can improve the speed and the precision at which an operator reams a bone to a calculated maximum cutting depth. As the depth limiter 114 can mechanically limit distal translation of the reamer 112, an operator can cut directly to the maximum cutting depth without concern for over-reaming, and as the depth limiter can be electronically configured using radiographic information obtained directly from preoperative and intraoperative fluoroscopy to limit distal translation of the reamer 112 without post-fluoroscopic movement of the robotic arm 102, the depth limiter 114 can help to improve the precision and consistency at which the reamer 112 is guided to the calculated maximum cutting depth without the use of anatomical tracking, while reducing risk to a patient, improving the probability of a successful implantation, and helping to reduce the time required to perform the implantation procedure.

Figure 2:
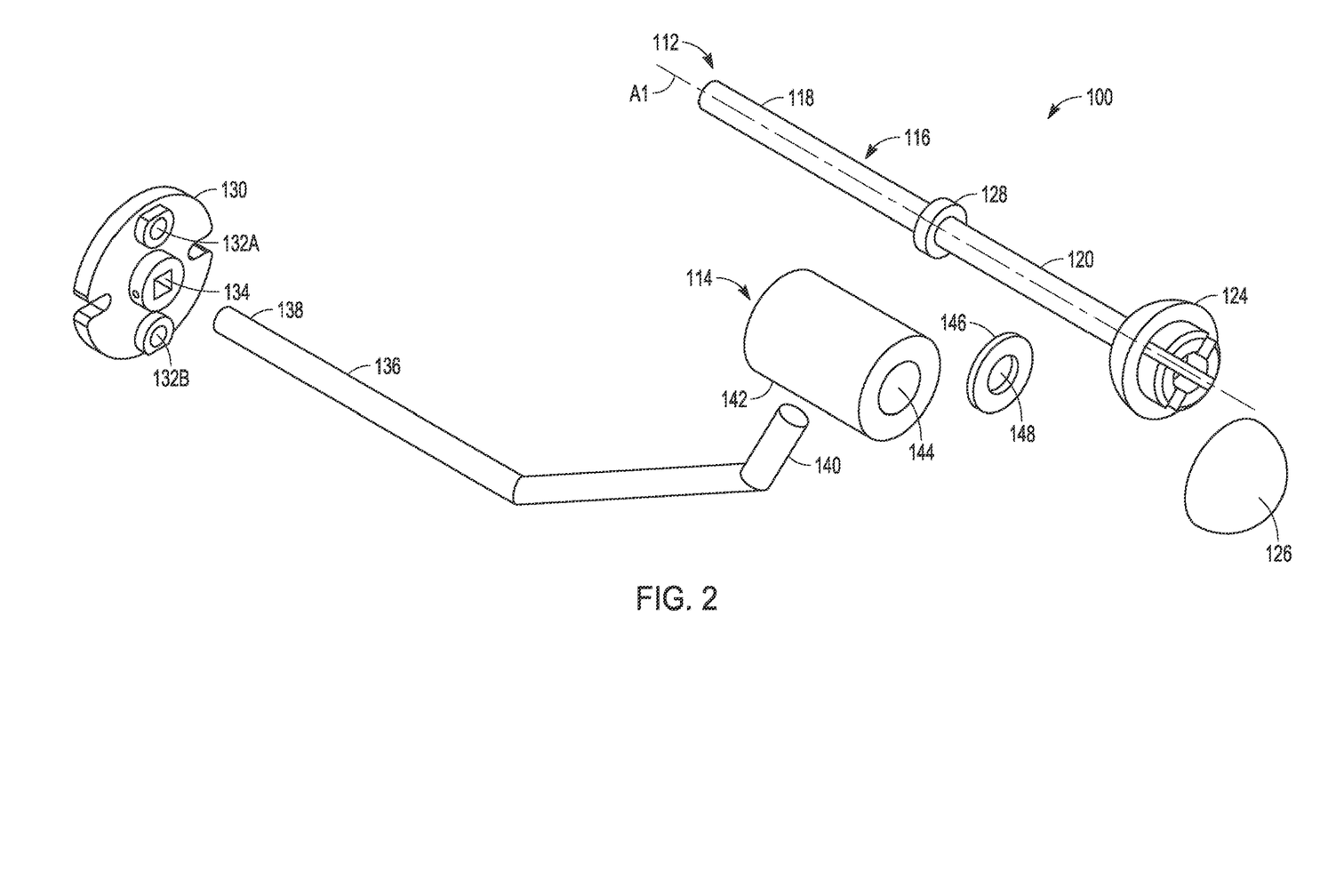
FIG. 2 illustrates an exploded isometric view of an example of an end effector including a reamer and depth limiter, in accordance with at least one example of the present application.

FIG. 2 illustrates an exploded view of an example of an end effector 100 including a reamer 112 and depth limiter 114, in accordance with at least one example of the present application. Also shown in FIG. 2 is a central axis A1. As illustrated in FIG. 2, the reamer 112 can include a driveshaft 116. The driveshaft 116 can define, extend along, and rotate around, the central axis A1. The driveshaft 116 can include a proximal portion 118 and a distal portion 120. The proximal portion 118 and the distal portion 120 can generally define opposite proximal and distal ends of the reamer 112. The distal portion 120 of the driveshaft 116 can include a coupler 124. The coupler 124 can extend radially outward and distally from the distal portion 120 of the driveshaft 116. The coupler 124 can be configured to engage a cutting head 126 to couple the cutting head 126 to the driveshaft 116.

The cutting head 126 can include cutting teeth, or other cutting or abrasive features. The cutting head 126 can form a generally cylindrical shape; but can also form other three-dimensional shapes in other examples. Different pre-existing types or styles of the cutting head 126 can be coupled to the driveshaft 116, such as intraoperatively (e.g., within the same surgery) to achieve different reaming effects or inter-operatively (e.g., between different surgeries) for cleaning, maintenance (e.g., sharpening) if the cutting elements become dull, sterilization, or disposal.

The driveshaft 116 can also include a protrusion 128 that can extend radially outward from the driveshaft 116 and can extend at least partially around a circumference of the driveshaft 116. The protrusion can have a generally cylindrical or elliptical shape, but can also form other three-dimensional shapes such as rectangles or cubes. The protrusion can be positioned on the driveshaft 116, between the proximal portion 118 and the distal portion 120. The coupler 124 can be integrally formed with the driveshaft 116 via machining or molding, or can be otherwise coupled to the driveshaft 116 via adhesives, welding, brazing, fasteners, or other methods. The protrusion 128 can be configured to engage the depth limiter 114, to help limit distal translation of the cutting head 126 along the central axis A1, such as when the driveshaft 116 is positioning within the depth limiter 114.

The end effector 100 (shown in FIGS. 1A and 1B) can include a tool base 130. The tool base 130 can engage a distal end of a robotic arm, such as the robotic arm 102 shown in FIGS. 1A and 1B. The tool base 130 can include mounting bores 132A and 132B that can engage with features on a robotic arm. The mounting bores 132A and 132B can be configured for various types of fasteners such as a threaded coupling, locking pins, or the like, to help couple the tool base 130 to a robotic arm. The mounting bores 132A and 132B can also align with features on a robotic arm, to ensure a proper mounting orientation of the tool base 130, relative to the robotic arm. The tool base 130 can also include retainer bore 134. The retainer bore 134 can be configured for various types of fasteners such as threaded coupling, locking pins, or a combination thereof. The retainer bore 134 can be configured to accept a retainer 136 of the end effector 100.

The retainer 136 can generally be a shaft or an arm. The retainer 136 can have a cylindrical shape, but the retainer 136 can also form other three-dimensional shapes. For example, the retainer 136 can be C-shaped, U-shaped, V-shaped, or a variety of other three-dimensional shapes. The retainer 136 can include a proximal end 138 and a distal end 140. The proximal end 138 of the retainer 136 can be configured to enter and contact the retainer bore 134 of the tool base 130 to couple the reamer 112 to the tool base 130, and thereby the robotic arm 102. The distal end 140 of the retainer 136 can be engageable with the depth limiter 114 to help couple the retainer 136 to the depth limiter 114. The distal end 140 of the retainer 136 can be configured for various types of fasteners such a threaded coupling, locking pins, adhesives, or a combination thereof to engage with the depth limiter 114.

The depth limiter 114 can include a housing 142. The housing 142 can be generally cylindrical in shape; but can also comprise other three-dimensional shapes such as rectangular prisms. The housing 142 can be coupled to the distal end 140 of the retainer 136 to couple the depth limiter 114 to the end effector 100. The housing 142 can define a bore 144 extending therethrough along the central axis A1. The bore 144 can be sized and shaped to accommodate and engage the depth stop 146. The depth stop 146 can generally be a cylinder or a disc configured to engage the protrusion 128 of the driveshaft 116. The depth stop 146 can be sized and shaped to slidably engage an inner wall of the housing 142; defined by the bore 144 of the housing 142. The housing 142 can thereby encompass a portion of the driveshaft 116 between the proximal portion 118 and the distal portion 120 of the driveshaft 116.

The depth stop 146 can define a shaft bore 148. The shaft bore 148 can also be configured to axially receive the driveshaft 116 of the reamer 112 therethrough. The shaft bore 148 can be configured to contact and engage the driveshaft 116, such that when the depth stop 146 is positioned within the bore 144 of the housing 142 and distally to the protrusion 128, the depth stop 146 can help limit distal translation of the driveshaft 116 by engaging the protrusion 128. Operation of the depth limiter 114 is discussed in further detail below with respect to FIG. 3.

The end effector 100, including the reamer 112, the depth limiter 114, the driveshaft 116, the protrusion 128, the coupler 124, the cutting head 126, the tool base 130, the retainer 136, the housing 142, the depth stop 146, and various components thereof, can each be made from, in an example, stainless steel, or other metals via machining or metallic molding or 3D printing. The end effector 100, including the reamer 112, the depth limiter 114, the driveshaft 116, the protrusion 128, the coupler 124, the cutting head 126, the tool base 130, the retainer 136, the housing 142, the depth stop 146, or certain components thereof, can each be made from plastics or other composites. For example, the components listed above can be molded, or otherwise made from, ABS plastic.

Figure 3:
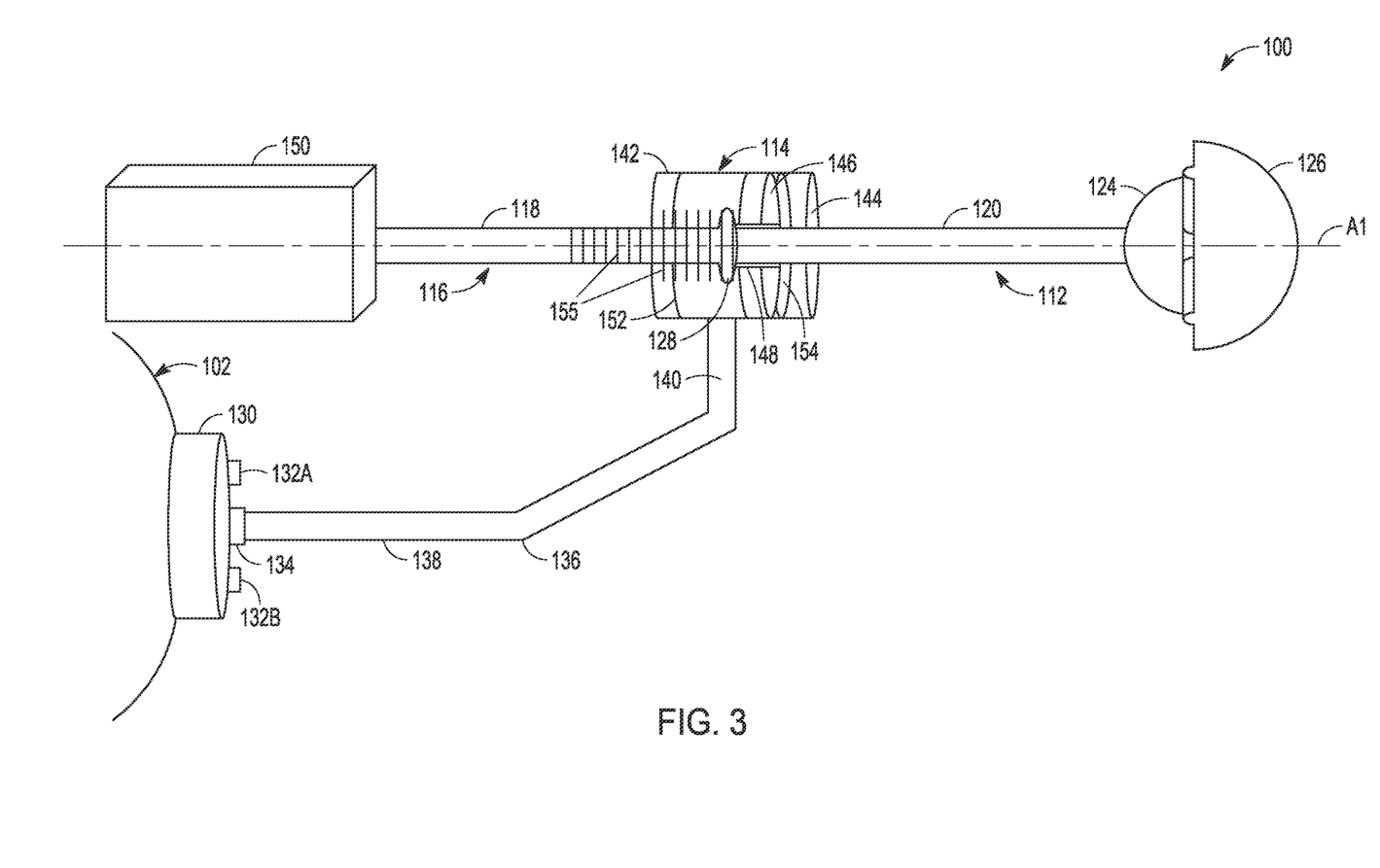
FIG. 3 illustrates a side isometric view of an end effector including a depth limiter and a reamer, in accordance with at least one example of the present application.

FIG. 3 illustrates a side isometric view of an end effector 100 including the depth limiter 114 and the reamer 112, in accordance with at least one example of the present application. Also shown in FIG. 3 is the central axis A1. As illustrated in FIG. 3, the proximal portion 118 of the driveshaft 116 can be coupled to a motive source 150, which can be an electric motor or a pneumatic motor configured to receive power, and be controlled by, a robotic arm and control system, such as the robotic arm 102 and the control system 104 shown in FIGS. 1A-1B. The motive source 150 can also be an external drive device not associated with a surgical arm, such as a handheld, electrically powered drill. The motive source 150 can rotate the driveshaft 116 around the central axis A1 to help provide rotational drive to the cutting head 126 of the reamer 112.

The tool base 130 can be coupled to the robotic arm 102 via mounting bores 132A and 132B. The proximal end 138 of the retainer 136 can be coupled to the tool base 130 within the retainer bore 134, and the distal end 140 of the retainer 136 can be coupled to the housing 142 of the depth limiter 114. The depth stop 146 can be located within the housing 142 of the depth limiter 114, such that the depth stop 146 contacts and engages the bore 144. The driveshaft 116 of the reamer 112 can be inserted into the depth limiter 114, such that a portion of the driveshaft 116 is encompassed by the cylindrical housing. The driveshaft 116 can be inserted in a proximal to distal direction, through the depth limiter 114, until the driveshaft 116 extends through the shaft bore 148 of the depth stop 146, and the protrusion 128 contacts the depth stop 146, limiting further distal translation of the driveshaft 116.

The depth stop 146, and correspondingly, the driveshaft 116 can be translated proximally or distally within the housing 142 of the depth limiter 114 to adjust a maximum cutting depth of the cutting head 126 coupled to the distal portion 120 of the driveshaft 116. The depth stop 146 can be electrically coupled to the processing circuitry of the control system 104 of the robotic arm 102. A user can thereby electrically translate the depth stop 146 axially, proximally or distally, within the housing 142 via the control system 104 of the robotic arm 102, shown in FIGS. 1A and 1B.

The control system 104 shown in FIG. 1A is also capable of automatically configuring the depth limiter 114, to translate the depth stop 146 within the housing 142 to a point corresponding to a maximum cutting depth. The depth limiter 114 can also include a linear encoder located within, or externally to, the housing 142. The linear encoder can be configured to monitor and communicate a position of the depth stop 146 within the housing 142 to the control system 104, processing circuitry of the control system 104. In some examples, the depth stop 146 can be manually adjustable by a user. For example, the housing 142 can include an external adjustment feature configured to allow a user to manually translate the depth stop 146 within the housing 142, such as a protrusion extending through the housing 142, a click wheel engageable with the depth stop 146, or other types of adjustment features.

In some examples, the housing 142 of the depth limiter 114 can include a first ridge 152 and a second ridge 154. The first ridge 152 and the second ridge 154 can be protrusions radially extending into the bore 144 of the housing 142, of the depth limiter 114. Alternatively, instead of protrusions, the first ridge 152 and the second ridge 154 can represent opposite proximal and distal ends of a cylindrical recess formed axially in the bore 144 of the housing 142 of the depth limiter 114. The first ridge 152 can be formed at or near a proximal end of the housing 142. The second ridge 154 can be formed at or near a proximal end of the housing 142. The first ridge 152 and the second ridge 154 can define maximum proximal and distal extension points for the depth stop 146, within the housing 142. The first ridge 152 and the second ridge 154 can thereby define a total potential length of the travel of the driveshaft 116 and the cutting head 126 when connected to the depth limiter 114. For example, the first ridge 152 can be spaced laterally apart along the central axis A1 from the second ridge 154 by 1-2 centimeters (cm), 2-5 cm, 6-15 cm, or 1-20 cm.

In the operation of some examples, a surgeon can align and position the robotic arm 102 within an access incision of a patient. The access incision can expose the hip joint, including the acetabulum. The surgeon can position the reamer 112 within the acetabulum, without activating the reamer 112. One or more fluoroscopic images can be taken, and the surgeon can input the resulting radiographic information, including the dimensions of the cutting head 126, into the control system 104, as shown in FIG. 1.

The control system 104 can display the information on the display screen 108, and a surgeon can use the information to calculate a desired maximum cutting depth in the acetabulum. The reamer 112 and the depth limiter 114 can also include scale markers 155. The scale markers 155 on the reamer 112 can be proportional to the scale markers 155 on the depth limiter 114, and can be visible on fluoroscopic images. The scale markers 155 can thereby help a surgeon to calculate the maximum cutting depth in the acetabulum.

Alternatively, the control system 104 can calculate the maximum cutting depth. The maximum cutting depth can then be entered using the control system 104, which can adjust the depth stop 146 by moving the depth stop 146 axially within the bore 144 of the housing 142 to correspond to the input maximum cutting depth in the acetabulum. In some examples, a surgeon can also manually adjust the depth stop 146 to correspond to the maximum cutting depth. Once the depth stop 146 is set, such as following a confirmation by the control system 104 or the surgeon, the surgeon can activate and translate the reamer 112 distally, along the central axis A1, to perform a cut of bone (such as the acetabulum) until the depth stop 146 engages the protrusion 128, helping to limit further axial translation of the driveshaft 116 and therefore helping to limit reaming beyond the maximum desired depth selected by the surgeon or the control system 104.

Additional images can be also taken and the maximum depth can be updated intraoperatively to ensure that the acetabulum is not-under reamed or over-reamed, such as due to intraoperative patient movement. Further, the control system 104 can also use the additional images to update on or more aspects of the radiographic imaging displayed to a surgeon on the display screen 108. For example, the control system 104 can indicate to a surgeon, through the display screen 108, specific portions of bone that have been removed by the reamer 112, based on the additional intraoperative images. For example, the control system 104 could shade or otherwise color portions of a radiographic image displayed on the display screen 108 corresponding to portions of a bone that have been removed.

Figure 4:
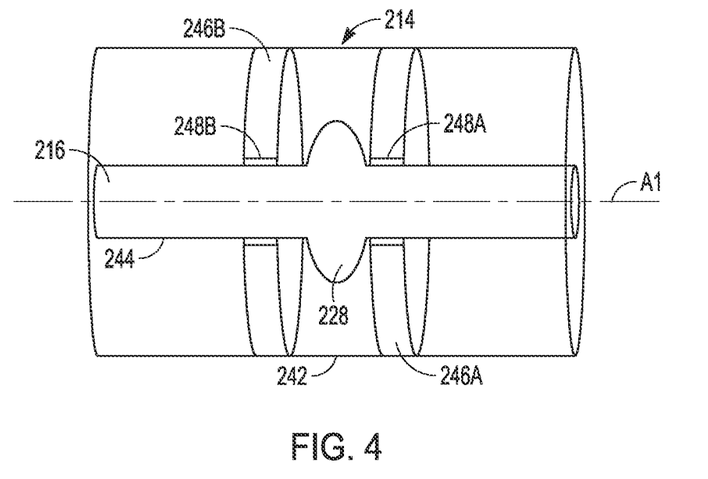
FIG. 4 illustrates an isometric view of an example of a depth limiter, in accordance with at least one example of the present application.

FIG. 4 illustrates an isometric view of an example of the depth limiter 214, in accordance with at least one example of the present application. As shown in FIG. 4 is a central axis A1. The depth limiter 214, including components thereof, can be similar to or interchangeable with the depth limiter 114, as shown in FIGS. 1-3. The depth limiter 214 can include a second depth stop. Any of the previously or later discussed depth limiters can be modified to include a second depth stop.

As illustrated in FIG. 4, the housing 242 of the depth limiter 214 is shown in phantom. The depth limiter 214 can include a first depth stop 246A including a first shaft bore 248A, and a second depth stop 246B including a second shaft bore 248B. The first depth stop 246A and the second depth stop 246B can be positioned within the bore 244 of the housing 242 of the depth limiter 214. The first depth stop 246A can be located distally to the protrusion 228 of the driveshaft 216, and the second depth stop 246B can be located proximally to the protrusion 228 of the driveshaft 216. By contacting both a proximal and a distal surface of the protrusion 228, the first depth stop 246A and the second depth stop 246B can together help to limit proximal translation and distal translation of the driveshaft 216 with respect to the housing 242. The second depth stop 246B can also help to axially positon the driveshaft 216 along the central axis A1 during proximal or distal translation, as both the first shaft bore 248A and the second shaft bore 248B can engage the driveshaft 116 to positon the driveshaft 116 along the central axis A1.

In some examples, the second depth stop 246B can be frangible to provide a surgeon with the option of distally translating the driveshaft 216 beyond the second depth stop 246B, during reaming, by applying pressure exceeding a maximum pressure of the second depth stop 246B, via the driveshaft 216. Alternatively, the driveshaft 216 and the second depth stop 246B can be removed from the housing 242 of the depth limiter 214. The second depth stop 246B can be separated from the driveshaft 216, and the driveshaft 216 can then be reinserted through the first shaft bore 248A of the first depth stop 246A and repositioned within the housing 242, to provide a surgeon with the option of distally translating the driveshaft 216 beyond the second depth stop 246B.

Figure 5:
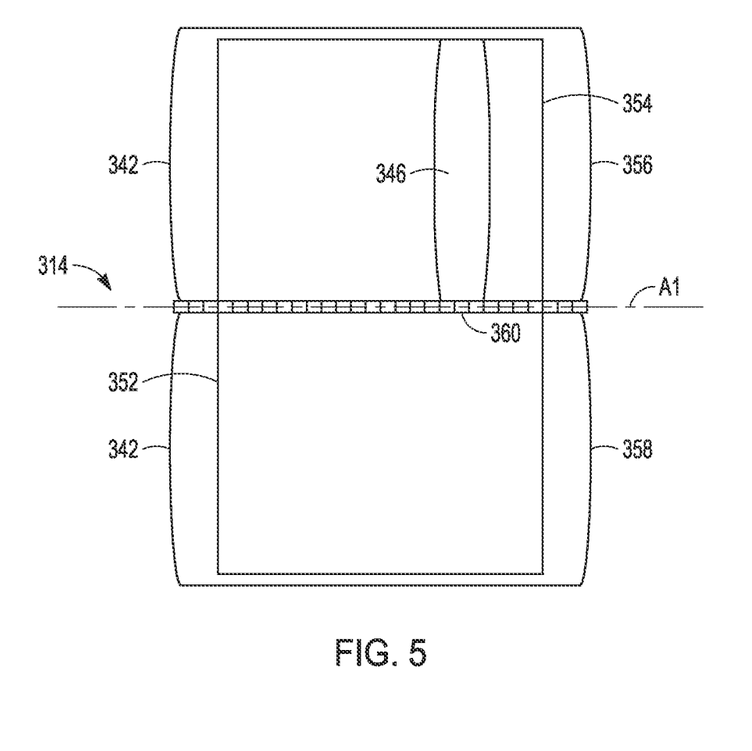
FIG. 5 illustrates an isometric view of an example of a depth limiter in an open position, in accordance with at least one example of the present application.

FIG. 5 illustrates an isometric view of an example of the depth limiter 314 in an open position, in accordance with at least one example of the present application. The depth limiter 314, including components thereof, can be similar to or interchangeable with the depth limiter 114 as shown in FIGS. 1-3, or the depth limiter 214 shown in FIG. 4. As shown in FIG. 5 is a central axis A1. The housing 342 of the depth limiter 314 can include a first portion and a second portion. Any of the previously or later discussed depth limiters can be modified to include first portion and a second portion.

As illustrated in FIG. 5, the housing 342 of the depth limiter 314 is shown in phantom. The depth limiter 314 can include a first portion 356 and a second portion 358. The first portion 356 and the second portion 358 can each be semi-cylindrical portions of the housing 342. For example, the first portion 356 can form a top portion and the second portion 358 can form a bottom portion. The first portion 356 and the second portion 358 can together comprise the housing 342. In some examples, the first portion 356 and the second portion 358 can also comprise a first ridge 352 and a second ridge 354.

The first portion 356 and the second portion 358 can be coupled with a hinge 360. Hinge leaves of the hinge 360 can extend along an outer surface of the first portion 356 and the second portion 358 of the housing 342. The hinge 360 can extend along the central axis A1; substantially along an entire length of the housing 342. The hinge 360 can also extend for substantially less than the entire length of the housing 342. The hinge 360 can aid a user in coupling the depth limiter 314 to a driveshaft of a reamer, in preparation for a surgical procedure; for example, the driveshaft 116 of the reamer 112 shown in FIGS. 2-3. Instead of translating the driveshaft 116 in a distal direction into the depth limiter 114, and subsequently attaching the coupler 124 and the cutting head 126 to the driveshaft 116, a user can operate the hinge 360 to open the housing 342. When the housing 342 is in an open position, a user can position the driveshaft 116 within the first portion 356 or the second portion 358 of the housing 342; positioning the protrusion 128 proximally to the depth stop 346 within the housing 342. A user can then operate the hinge 360 to close the housing 342, to retain the driveshaft 116 within the housing 342.

Figure 6:
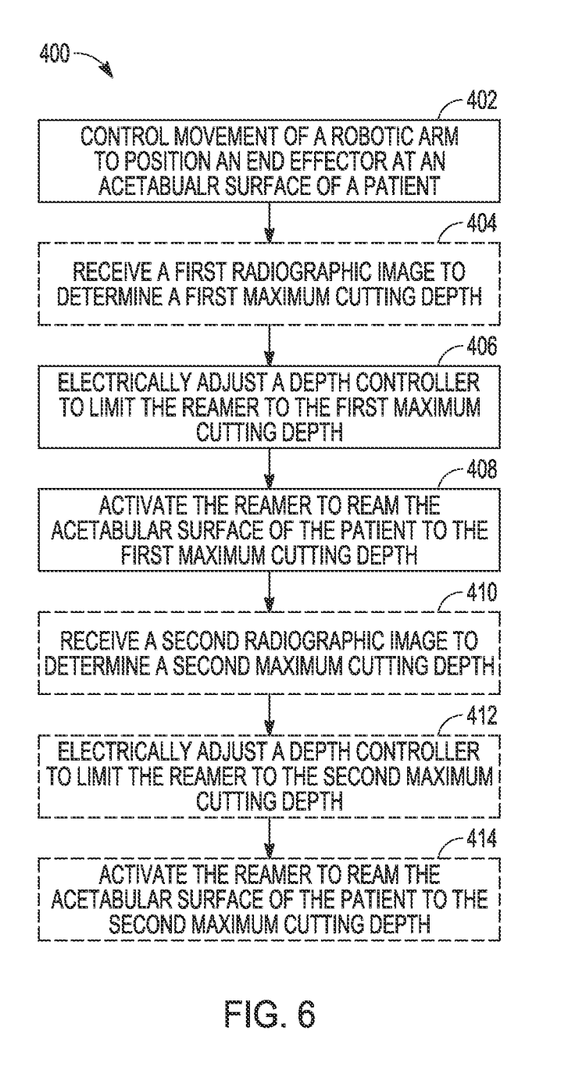
FIG. 6 illustrates an example of a method of robotically controlling a reamer, in accordance with at least one example of the present application.

FIG. 6 illustrates an example of a method of robotically controlling a reamer, in accordance with at least one example of the present application. The steps or operations of the method 400 are illustrated in a particular order for convenience and clarity, the discussed operations can be performed in parallel or in a different sequence without materially impacting other operations. The method 400 as discussed includes operations that can be performed by multiple different actors, devices, and/or systems. It is understood that subsets of the operations discussed in the method 400 can be attributable to a single actor device, or system, and could be considered a separate standalone process or method.

The method 400 includes an operation 402 to, using processing circuitry, control movement of a robotic arm to position an end effector at an acetabular surface of a patient. For example, a user can control the robotic arm using a control system, to position the end effector, including a reamer at an acetabular surface of a patient, within an access incision.

The method 400 includes an operation 404 to receive a first radiographic image to determine a first maximum cutting depth. For example, a user can calculate a first maximum cutting depth in the acetabular surface of the patient, by taking a fluoroscopic image of the cutting head of the reamer positioned at an acetabular surface of a patient, to determine a first maximum cutting depth in the acetabular surface based on the scale of a cutting head of the reamer, and the location of the cutting head, relative to the acetabular surface. The first maximum cutting depth can also be determined by processing circuitry of the control system of the robotic arm.

The method 400 includes an operation 406 to use processing circuitry, to electrically adjust a depth controller to limit the reamer to the first maximum cutting depth. For example, a user can input the first maximum cutting depth into the control system of the robotic arm. The control system can automatically, using processing circuitry, translate the depth stop proximally or distally within the housing of the depth limiter, to configure the depth limiter to limit distal translation of the cutting head of the reamer to the first maximum cutting depth without adjusting a position of the robotic arm.

The method 400 includes an operation 408 to activate the reamer to ream the acetabular surface of the patient to the first maximum cutting depth. For example, a user can activate the reamer, using the control system of the robotic arm, and manually translate the driveshaft of the reamer in a distal direction, to bring the cutting head into contact with a patient's acetabular surface. A user can further translate the cutting head distally until the protrusion of the driveshaft contacts the depth stop, preventing further translation of the cutting head and thereby limiting the reaming of the acetabular surface to the first maximum cutting depth. A user can also use the control system to operate the robotic arm to translate the end effector, including the reamer, to bring the cutting head into contact with a patient's acetabular surface.

The method 400 can optionally include an operation 410 to receive a second radiographic image to determine a second maximum cutting depth. For example, a user can calculate a second maximum cutting depth in the acetabular surface of the patient, by taking a fluoroscopic image of the cutting head of the reamer positioned at an acetabular surface of a patient, to determine a second maximum cutting depth in the acetabular surface based on the scale of a cutting head of the reamer, and the location of the cutting head, relative to the acetabular surface. The second maximum cutting depth can also be determined by processing circuitry of the control system of the robotic arm.

The method 400 can optionally include an operation 412 to processing circuitry, to electrically adjust a depth controller to limit the reamer to the second maximum cutting depth. For example, a user can input the second maximum cutting depth into the control system of the robotic arm. The control system can automatically, using processing circuitry, translate the depth stop proximally or distally within the housing of the depth limiter, to configure the depth limiter to limit distal translation of the cutting head of the reamer to the second maximum cutting depth.

The method 400 can optionally include an operation 414 to activate the reamer to ream the acetabular surface of the patient to the second maximum cutting depth. For example, a user can activate the reamer, using the control system of the robotic arm, and manually translate the driveshaft of the reamer in a distal direction, to bring the cutting head into contact with a patient's acetabular surface. A user can further translate the cutting head distally until the protrusion of the driveshaft contacts the depth stop, preventing further translation of the cutting head and thereby limiting the reaming of the acetabular surface to the second maximum cutting depth. A user can also use the control system to operate the robotic arm to translate the end effector, including the reamer, to bring the cutting head into contact with a patient's acetabular surface.

Figure 7:
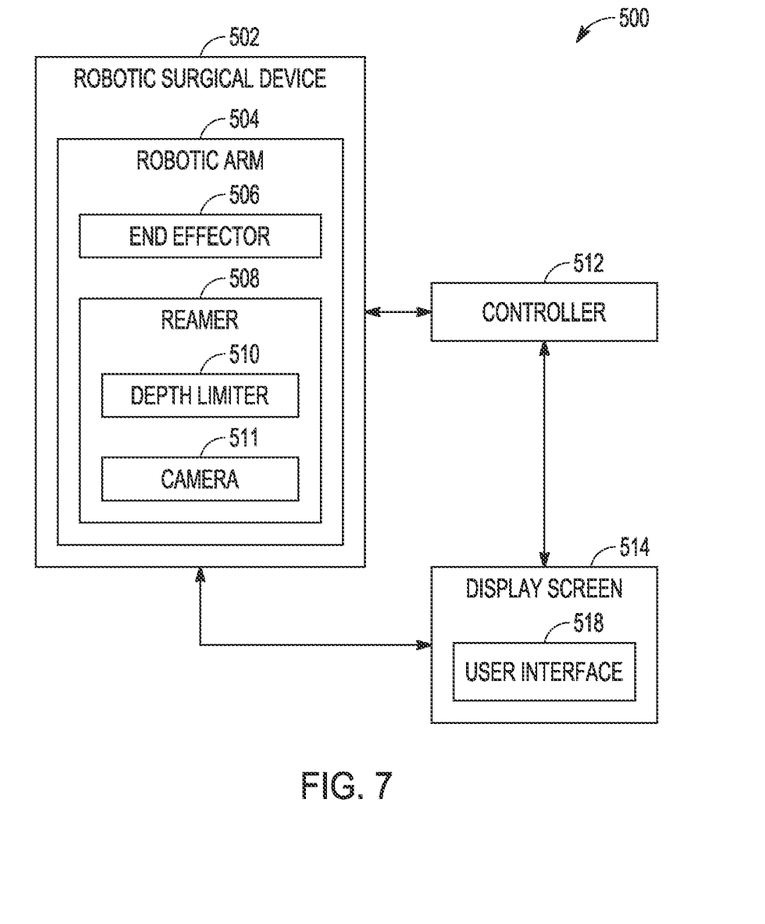
FIG. 7 illustrates a schematic view of a system for robotically assisted reaming, in accordance with at least one example of the present application.

FIG. 7 illustrates a schematic view of a robotic surgical system 500 for robotically assisted reaming, in accordance with at least one example of the present application. The robotic surgical system 500 includes a robotic surgical device 502, which can include a robotic arm 504, an end effector 506, a reamer 508, and a depth limiter 510. The robotic arm 504 can be similar to the robotic arm 102 discussed above with respect to FIGS. 1A and 1B, in that the robotic arm 504 can be a movable and articulable robotic arm. The end effector 506 can be similar to the end effector 100 discussed with respect to FIGS. 1-3 above.

The robotic arm 504 can move autonomously in an example. In another example, the robotic arm 504 can provide a force assist or a force resistance to surgeon or user guided movements. In yet another example, a combination of autonomous movement and force assistance or force resistance movement can be performed by the robotic arm 504 (e.g., force assistance or force resistance for an initial movement, and autonomously moving a later movement). In an example, the robotic arm 504 can resist an applied force. For example, the robotic arm 504 can be programmed to stay within a particular range of locations or a particular position, move at a particular speed (e.g., resist a higher speed by resisting force), or the like.

The robotic surgical device 502 can output or receive data from a controller 512. The controller 512 can be implemented in processing circuitry (e.g., hardwired or a processor), a programmable controller, such as a single or multi-board computer, a direct digital controller (DDC), a programmable logic controller (PLC), a system on a chip, a mobile device (e.g., cell phone or tablet), a computer, or the like. In one example, the controller 512 can output information to a display screen 514. The display screen 514 can retrieve and display information from an imaging camera 511. The imaging camera 511 can be an optical navigation camera physically positioned on the robotic surgical device 502, such as on the robotic arm 504, the end effector 506, the reamer 508, or the depth limiter 510. The imaging camera 511 can also be a C-arm or O-arm, to capture intraoperative fluoroscopic images. In an example, the display screen 514 can be used to display a user interface 518. In an example, the display screen 514 can be a touch screen display. In another example, user interface 518 on the display screen 514 can provide lights, buttons, or switches. A user can interact with the display screen 514 and the user interface 518 to input control commands, which can be relayed to the robotic surgical device 502 through the controller 512 to control the robotic surgical device 502. The robotic surgical system 500 can be used to perform all, or a portion of, a surgical procedure on a patient.

In the operation of some examples, a user can interact with the user interface 518 on the display screen 514 to power on the robotic surgical device 502. Power can be indicated by a light, for example, on the user interface 518, or on the robotic arm 504. When the robotic surgical device 502 is powered on, the user can operate the robotic arm 504 to operate the end effector 506, the reamer 508, and the depth limiter 510 by interacting with the display screen 514 and the user interface 518. The robotic arm 504 can additionally include a camera or ultrasonic transducer affixed to an end of the reamer 508 (e.g., at a cutting or a housing of the cutting head) to provide additional information to a user through the display screen 514. The robotic arm 504 can also be configured to resist movement of the robotic arm 504 (e.g., to prevent translation or rotation by the reamer 508) from a force applied by a motor, for example, and electrical motor providing rotational drive to the reamer 508.

The robotic surgical system 500 can be used to ream a target bone surface of a patient to prepare the target bone surface to receive an implant. In an example, a cutting angle, trajectory of the cutting head of the reamer 508 can be changed intraoperatively, for example using the controller 512, in contrast to non-adjustable methods of guiding reamers, such a guide pin fixed to the bone. In another example, a maximum cutting depth of the reamer 508 can be controlled and changed intra-operatively, for example using the controller 512 to adjust the robotic arm 504 or the depth limiter 510, in contrast to traditional hand-held reamers requiring a manual or non-adjustable depth stop. The bone penetration depth of the reamer 508 can be also be precisely controlled using the depth limiter 510, by using radiographic images to adjust the depth limiter 510, in contrast to a hand-held reamer guided by purely visual input.

The robotic surgical system 500 may be configured to use the reamer 508 to ream bone. The reamer 508 can be coupled to the end effector 506. The reamer 508 can include a driveshaft. The depth limiter 510 can include a cylindrical housing configured to encompass a portion of the driveshaft of the reamer 508. The depth limiter 510 can include a depth stop engaging the cylindrical housing within the bore and defining an opening configured to receive the driveshaft of the reamer 508 therethrough. The depth stop can be configured to receive a signal via processing circuitry of the robotic arm 504, to operate the depth stop to limit distal translation of the driveshaft relative to the cylindrical housing, by mechanically engaging a protrusion on the driveshaft to control a maximum cutting depth of the reamer.

For example, the controller 512 can receive dimensions of a reamer and a maximum cutting depth or depth range based on radiographic information, identify a current depth, and act to prevent further translation, using the depth limiter 510, of the reamer 508, by robotic arm 504 or by the hand of a surgeon, when the current depth of the reamer 508 approaches or reaches the maximum cutting depth or depth range. The depth range or the maximum cutting depth can be determined pre-operatively during a pre-operative planning stage, in an example, or intraoperatively, in another example. Determining the maximum cutting depth or depth range can include taking one or more fluoroscopic images of the reamer 508 when positioned at a patient's acetabulum or acetabular cavity, to identify the maximum cutting depth or depth range.

Figure 8:
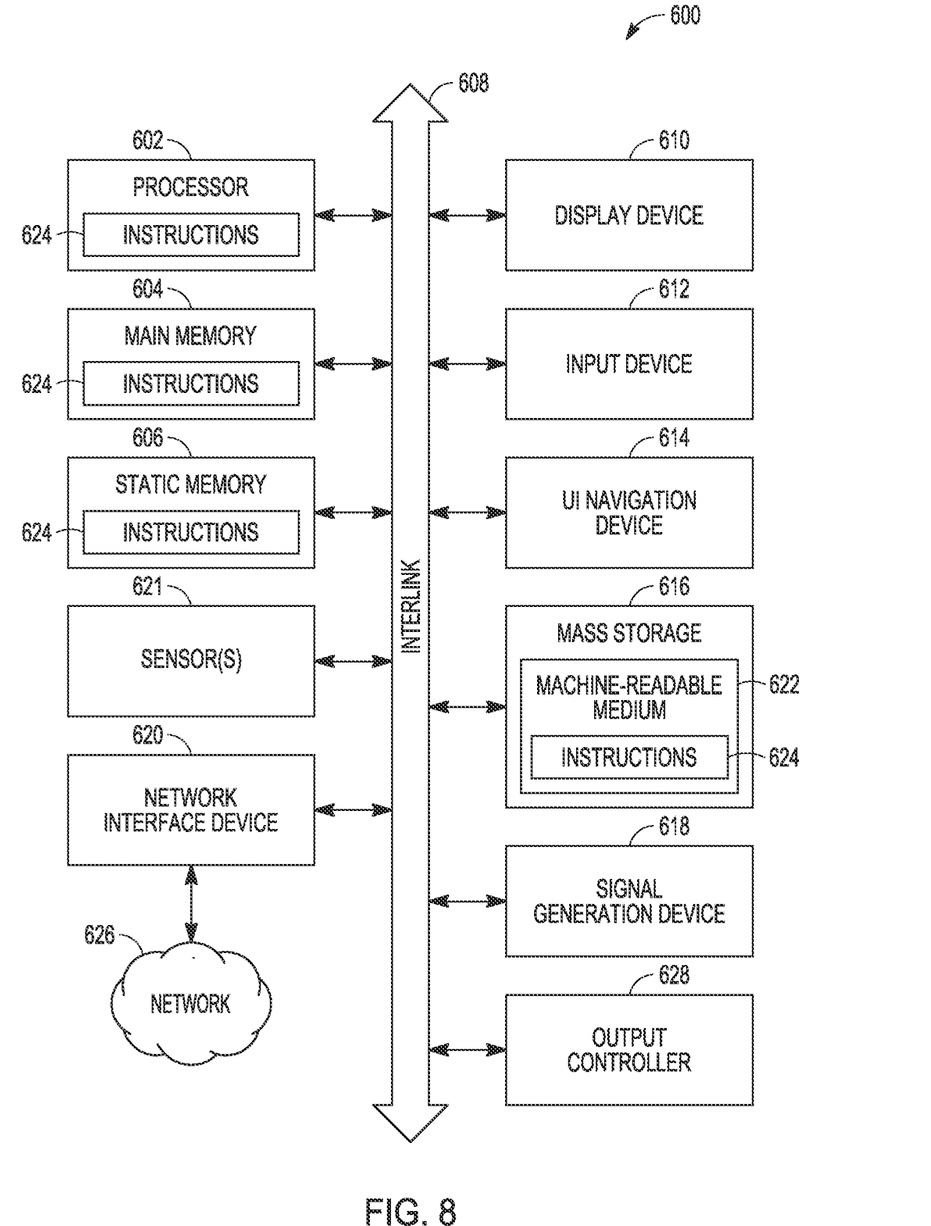
FIG. 8 illustrates a block diagram of an example machine upon which any one or more of the techniques discussed herein can be performed, in accordance with at least one example of the present application.

FIG. 8 illustrates a block diagram of an example machine 600 upon which any one or more of the techniques discussed herein can perform in accordance with some embodiments. In alternative embodiments, the machine 600 can operate as a standalone device or can be connected (e.g., networked) to other machines. In a networked deployment, the machine 600 can operate in the capacity of a server machine, a client machine, or both in server-client network environments. In an example, the machine 600 can act as a peer machine in peer-to-peer (P2P) (or other distributed) network environment.

The machine 600 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 600 can include a hardware processor 602 (e.g., a central processing unit (CPU), a graphics processing unit (GPU), a hardware processor core, or any combination thereof), a main memory 604 and a static memory 606, some or all of which can communicate with each other via an interlink (e.g., bus) 608. The machine 600 can further include a display unit 610, an alphanumeric input device 612 (e.g., a keyboard), and a user interface (UI) navigation device 614 (e.g., a mouse). In an example, the display unit 610, input device 612 and UI navigation device 614 can be a touch screen display. The machine 600 can additionally include a storage device (e.g., drive unit) 616, a signal generation device 618 (e.g., a speaker), a network interface device 620, and one or more sensors 621, such as a global positioning system (GPS) sensor, compass, accelerometer, or other sensors. The machine 600 can include an output controller 628, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 616 can include a machine readable medium 622 on which is stored one or more sets of data structures or instructions 624 (e.g., software) embodying or utilized by any one or more of the techniques or functions described herein. The instructions 624 can also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 can constitute machine readable media.

While the machine readable medium 622 is illustrated as a single medium, the term "machine readable medium" can include a single medium or multiple media (e.g., a centralized or distributed database, or associated caches and servers) configured to store the one or more instructions 624. The term "machine readable medium" can include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples can include solid-state memories, and optical and magnetic media.

The instructions 624 can further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 can include one or more physical jacks (e.g., Ethernet, coaxial, or phone jacks) or one or more antennas to connect to the communications network 626.

In an example, the network interface device 620 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

The following, non-limiting examples, detail certain aspects of the present subject matter to solve the challenges and provide the benefits discussed herein, among others.

Example 1 is a robotically controlled depth limiter for a reamer, the depth limiter comprising: a cylindrical housing configured to encompass a portion of a driveshaft of a reamer, the cylindrical housing defining a bore extending therethrough; a depth stop engaging the cylindrical housing within the bore and defining an opening configured to receive the driveshaft of the reamer therethrough, the depth stop configured to receive a signal via processing circuitry of a robotic arm, to operate the depth stop to engage the driveshaft to limit distal translation of the driveshaft relative to the cylindrical housing and to control a cutting depth of the reamer.

In Example 2, the subject matter of Example 1 includes, a protrusion extending radially outward from the driveshaft within the depth stop, the protrusion configured to engage a proximal or a distal end of the depth stop, to limit distal translation of the driveshaft within the cylindrical housing to control the cutting depth of the cutting head.

In Example 3, the subject matter of Examples 1-2 includes, wherein the cylindrical housing and the bore are comprised of a first portion and a second portion, the first portion and the second portion each defining a semi-cylindrical portion of the cylindrical housing.

In Example 4, the subject matter of Example 3 includes, wherein the first portion and the second portion of the cylindrical housing are coupled with a hinge, the hinge extending axially along a longitudinal length of the first portion and the second portion.

In Example 5, the subject matter of Examples 1-4 includes, wherein the depth stop includes a first and a second disc slideably positioned within the bore of the cylindrical housing, the first disc and the second disc spaced laterally apart, wherein the first disc is positioned distally to the protrusion of the driveshaft and the second disc is positioned proximally to the protrusion of the driveshaft.

Example 6 is a robotic surgical system comprising: a reamer including a driveshaft, the driveshaft including a protrusion extending radially outward from the driveshaft; a depth limiter including: a cylindrical housing configured to encompass a portion of a driveshaft of a reamer, the cylindrical housing defining a bore extending therethrough; a depth stop engaging the cylindrical housing within the bore and defining an opening configured to receive the driveshaft of the reamer therethrough, the driveshaft configured to rotate via a motor and including a cutting head extending from a distal end of the driveshaft; and a robotic arm including an end effector, the end effector including the reamer, the robotic arm including processing circuitry configured to operate the depth stop to engage the driveshaft to limit distal translation of the driveshaft relative to the cylindrical housing and to control a cutting depth of the cutting head.

In Example 7, the subject matter of Example 6 includes, wherein the cylindrical housing and the bore are comprised of a first portion and a second portion, the first portion and the second portion each defining a semi-cylindrical portion of the cylindrical housing.

In Example 8, the subject matter of Examples 6-7 includes, wherein the first portion and the second portion of the cylindrical housing of the depth limiter are coupled with a hinge, the hinge extending axially along a longitudinal length of the first portion and the second portion.

In Example 9, the subject matter of Examples 6-8 includes, wherein the depth stop includes a first and a second disc slideably positioned within the bore of the cylindrical housing of the depth limiter, the first disc and the second disc spaced laterally apart, wherein the first disc is positioned distally to the protrusion of the driveshaft and the second disc is positioned proximally to the protrusion of the driveshaft.

In Example 10, the subject matter of Examples 6-9 includes, wherein the depth stop of the depth limiter is detachably coupled to the end effector of the robotic arm with a retainer extending radially outward from an outer surface of the cylindrical housing of the depth stop.

In Example 11, the subject matter of Examples 6-10 includes, wherein the depth stop of the depth limiter is manually translatable, proximally and distally, within the bore of the cylindrical housing to adjustably control the cutting depth of the cutting head of the reamer.

In Example 12, the subject matter of Examples 6-11 includes, wherein the depth stop of the depth limiter is electrically translatable proximally and distally, using the processing circuitry of the robotic arm, within the bore of the cylindrical housing to adjustably control the cutting depth of the cutting head of the reamer.

In Example 13, the subject matter of Example 12 includes, a linear encoder, the linear encoder configured to monitor a position of the depth stop within the bore of the cylindrical housing and communicate the position of the depth stop to a user using the processing circuitry of the robotic arm.

In Example 14, the subject matter of Examples 6-13 includes, wherein the motor is an electric motor, wherein the motor is user-operable using the processing circuitry of the robotic arm.

In Example 15, the subject matter of Examples 6-14 includes, wherein the motor is a pneumatically-actuated motor, wherein the motor is user-operable using the processing circuitry of the robotic arm.

In Example 16, the subject matter of Examples 6-15 includes, wherein the robotic arm is configured to resist movement of the robotic arm from torque applied to the driveshaft of the reamer by the motor.

In Example 17, the subject matter of Examples 6-16 includes, wherein the robotic arm is configured to control the cutting depth of the cutting head of the reamer by using a camera affixed to the cutting head.

Example 18 is a method of robotically controlling a reamer, the method comprising: using processing circuitry, controlling movement of a robotic arm to position an end effector affixed to a distal end of the robotic arm at an acetabular surface of a patient, the end effector including a reamer extending distally therefrom; and receiving a first radiographic image of the reamer and the acetabular surface of the patient to determine a first maximum cutting depth in the acetabular surface, and using the processing circuitry, electrically adjusting, based on the first radiographic image, a depth controller coupled to the reamer, to configure the depth controller to limit a maximum cutting depth of the reamer to the first maximum cutting depth.

In Example 19, the subject matter of Example 18 includes, activating the reamer to ream the acetabular surface of the patient to the first maximum cutting depth.

In Example 20, the subject matter of Example 19 includes, receiving a second radiographic image of the reamer and the acetabular surface of the patient, to determine a second maximum cutting depth in the acetabular surface.

In Example 21, the subject matter of Example 20 includes, using the processing circuitry, electrically adjusting, based on the second radiographic image, the depth controller coupled to the reamer, to configure the reamer to limit the maximum cutting depth of the reamer to the second maximum cutting depth.

In Example 22, the subject matter of Example 21 includes, activating the reamer to ream the acetabular surface of the patient to the second maximum cutting depth.

In Example 23, the subject matter of Examples 18-22 includes, wherein controlling the robotic arm to position an end effector affixed to a distal end of the robotic arm near an acetabular surface of a patient includes using a camera affixed to the reamer.

Example 24 is a method of robotically controlling an impactor, the method comprising: using processing circuitry, controlling movement of a robotic arm to position an end effector affixed to a distal end of the robotic arm at an acetabular surface of a patient, the end effector including an impactor extending distally therefrom; and receiving a first radiographic image of the reamer and the acetabular surface of the patient to determine a first maximum impaction depth in the acetabular surface; and using the processing circuitry, electrically adjusting, based on the first radiographic image, a depth controller coupled to the impactor, to configure the depth controller to limit a maximum impacting depth of the impactor to the first maximum impaction depth.

Example 25 is a method of robotically controlling a reamer, the method comprising: using processing circuitry, controlling movement of a robotic arm to position an end effector affixed to a distal end of the robotic arm at an acetabular surface of a patient, the end effector including a reamer extending distally therefrom; receiving a first radiographic image of the reamer and the acetabular surface of the patient to determine a first maximum cutting depth in the acetabular surface; and manually adjusting, based on the first radiographic image, a depth controller coupled to the reamer, to configure the depth controller to limit a maximum cutting depth of the reamer to the first maximum cutting depth.

In Example 26, the subject matter of Example 25 includes, activating the reamer to ream the acetabular surface of the patient to the first maximum cutting depth.

Example 27 is at least one machine-readable medium including instructions that, when executed by processing circuitry, cause the processing circuitry to perform operations to implement of any of Examples 1-24.

Example 28 is an apparatus comprising means to implement of any of Examples 1-24.

Example 29 is a system to implement of any of Examples 1-24.

Example 30 is a method to implement of any of Examples 1-24.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A robotically controlled depth limiter for a reamer, the depth limiter comprising:
   a cylindrical housing configured to encompass a portion of a driveshaft of a reamer, the cylindrical housing defining a bore extending therethrough; and
   a depth stop engaging the cylindrical housing within the bore and defining an opening configured to receive the driveshaft of the reamer therethrough, the depth stop configured to receive a signal via processing circuitry of a robotic arm, to operate the depth stop to engage the driveshaft to limit distal translation of the driveshaft relative to the cylindrical housing and to control a cutting depth of the reamer.

2. The robotically controlled depth limiter of claim 1, wherein the depth stop is configured such that engagement between a protrusion extending radially outward from the driveshaft and a proximal or a distal end of the depth stop limits distal translation of the driveshaft within the cylindrical housing to control the cutting depth of the reamer.

3. The robotically controlled depth limiter of claim 1, wherein the cylindrical housing and the bore are comprised of a first portion and a second portion, the first portion and the second portion each defining a semi-cylindrical portion of the cylindrical housing.

4. The robotically controlled depth limiter of claim 3, wherein the first portion and the second portion of the cylindrical housing are coupled with a hinge, the hinge extending axially along a longitudinal length of the first portion and the second portion.

5. The robotically controlled depth limiter of claim 1, wherein the depth stop includes a first and a second disc slideably positioned within the bore of the cylindrical housing, the first disc and the second disc spaced laterally apart, wherein the first disc is configured to be positioned distally to a protrusion of the driveshaft and the second disc is configured to be positioned proximally to the protrusion of the driveshaft.

6. A robotic surgical system comprising:
a reamer including a driveshaft, the driveshaft including a protrusion extending radially outward from the driveshaft;
a depth limiter including:
a cylindrical housing configured to encompass a portion of the driveshaft of the reamer, the cylindrical housing defining a bore extending therethrough;
a depth stop engaging the cylindrical housing within the bore and defining an opening configured to receive the driveshaft of the reamer therethrough, the driveshaft configured to rotate via a motor and including a cutting head extending from a distal end of the driveshaft; and
a robotic arm including an end effector, the end effector including the reamer, the robotic arm including processing circuitry configured to operate the depth stop to engage the driveshaft to limit distal translation of the driveshaft relative to the cylindrical housing and to control a cutting depth of the cutting head.

7. The robotic surgical system of claim 6, wherein the cylindrical housing and the bore are comprised of a first portion and a second portion, the first portion and the second portion each defining a semi-cylindrical portion of the cylindrical housing.

8. The robotic surgical system of claim 7, wherein the first portion and the second portion of the cylindrical housing of the depth limiter are coupled with a hinge, the hinge extending axially along a longitudinal length of the first portion and the second portion.

9. The robotic surgical system of claim 6, wherein the depth stop includes a first and a second disc slideably positioned within the bore of the cylindrical housing of the depth limiter, the first disc and the second disc spaced laterally apart, wherein the first disc is positioned distally to the protrusion of the driveshaft and the second disc is positioned proximally to the protrusion of the driveshaft.

10. The robotic surgical system of claim 6, wherein the depth stop of the depth limiter is detachably coupled to the end effector of the robotic arm with a retainer extending radially outward from an outer surface of the cylindrical housing of the depth stop.

11. The robotic surgical system of claim 6, wherein the depth stop of the depth limiter is manually translatable, proximally and distally, within the bore of the cylindrical housing to adjustably control the cutting depth of the cutting head of the reamer.

12. The robotic surgical system of claim 6, wherein the depth stop of the depth limiter is electrically translatable proximally and distally, using the processing circuitry of the robotic arm, within the bore of the cylindrical housing to adjustably control the cutting depth of the cutting head of the reamer.

13. The robotic surgical system of claim 12, further comprising a linear encoder, the linear encoder configured to monitor a position of the depth stop within the bore of the cylindrical housing and communicate the position of the depth stop to a user using the processing circuitry of the robotic arm.

14. The robotic surgical system of claim 6, wherein the motor is an electric motor, wherein the motor is user-operable using the processing circuitry of the robotic arm.

15. The robotic surgical system of claim 6, wherein the motor is a pneumatically-actuated motor, wherein the motor is user-operable using the processing circuitry of the robotic arm.

16. The robotic surgical system of claim 6, wherein the robotic arm is configured to resist movement of the robotic arm from torque applied to the driveshaft of the reamer by the motor.

17. The robotic surgical system of claim 6, wherein the robotic arm is configured to control the cutting depth of the cutting head of the reamer by using a camera affixed to the cutting head.

* * * * *